United States Patent [19]

Driesener

[11] Patent Number: 5,190,458

[45] Date of Patent: Mar. 2, 1993

[54] CHARACTER ASSESSMENT METHOD

[76] Inventor: Valma R. Driesener, 13 Augusta Street, Maylands, Australia, 5069

[21] Appl. No.: 686,475

[22] Filed: Apr. 17, 1991

[30] Foreign Application Priority Data

Apr. 17, 1990 [AU] Australia ................ PJ9621

[51] Int. Cl.$^5$ ............................................. G09B 19/00
[52] U.S. Cl. ................................. 434/236; 434/433
[58] Field of Search ............................. 434/236, 433

[56] References Cited

PUBLICATIONS

"How to Really Know Yourself Through Your Handwriting", Shirl Solomon, 1974.

*Primary Examiner*—John G. Weiss
*Assistant Examiner*—L. Thomas
*Attorney, Agent, or Firm*—Cushman, Darby & Cushman

[57] ABSTRACT

A psychological test for character assessment, derived from a drawing drawn by an individual being instructed to include in the drawing a number of set graphic symbols. The graphic symbols are to be selected from the group including a hand, eye, tree, fish, star, spiral, half-circle and zig-zag. Further symbols may also be used such as flower, sun, bird and wave. Such symbols of the drawings are to be interconnected, and the heaviness of the line used and the sequence of drawing the symbols is preferably recorded. The information recorded and the drawing is used to provide information about the patterning or profile of the person tested.

9 Claims, 2 Drawing Sheets

CHARACTER ASSESSMENT METHOD

BACKGROUND OF THE INVENTION

This invention relates to a character assessment method.

The invention arises from the discovery that some words connect within a human to involuntary traits which can be exposed and interpreted when the subject attempts to replicate those words as symbols as a drawn work of art.

SUMMARY OF THE INVENTION

It has been discovered for instance that certain words are interpreted by a first hemisphere of the subject which is then re-interpreted from the logical hemisphere to the emotional hemisphere in so far that such words have to be replicated as an art form that the art work itself then carries a number of traits exposed by the emotional hemisphere in an apparently involuntary manner.

The method of the invention therefore is to provide a subject with instructions in relation to a plurality of words that identify interpretable characteristics in art form, and have the subject then replicate such instructions in an art form.

My discovery in particular is that there appears to be a small number of such words identifying symbols which correlate with other and sometimes quite unexpected characteristics of the alternate hemisphere from that accepting in a logical manner the instructions, and that in so far that such symbols can be recognised on a drawn page, be interpreted and provide means for psychological assessment.

In experiments conducted thus far, such assessments that now appear to be possible have shown to be of substantial value and to provide information about the patterning or profile of the subject and to some extent historical happenings which may not be able to be gained in any other manner.

It is considered the method of assessment therefore has some value for personnel selection, evaluation and it may have some value for therapeutic purposes.

One of the significant values of the method is that it requires very little time of the subject being tested, its basis will not normally be understood by a subject to enable easy falsification of the results, and the test can be conducted very easily but remotely without the assessor ever having met the subject.

Results thus far indicate a very high correlation between predicted characteristics of the subject and history of trauma and wishes and significant life events and actual occurrences history and events.

The way in which it seems to work is that is a way in which a word which comprises interpretable letters is interpretable by the logic hemisphere of the subject which then is required to transfer the information to the opposite hemisphere for a creative drawing.

I have discovered that a relatively small number of words identify concepts which when translated into graphic representations carry with them relevances which are not apparent to the human subject.

The invention in one form can be said to reside in a method of psychological testing comprising the steps of instructing a person to be tested with a set of words which require the person to draw a drawing incorporating in graphic form at least a majority of the symbols selected from the following words; a hand, eye, tree, fish, star, spiral, half-circle and zig-zag, and the person effecting a drawing following such instructions.

In the alternative, instructions further include the words "flower, sun, bird and wave".

In the alternate, the method includes the steps of instructing the person to use all of the symbols corresponding to all of the respective words.

Factors in a drawing which are of significant assistance include the direction in which a particular symbol or symbols are drawn so that it is desirable to have a record of where a particular symbol started and finished and it is also useful to have the drawing drawn with a medium such as a pencil that allows for the assessment to be able to pick up stronger or heavier impressions and lighter impressions.

A further useful characteristic is to know whether the subject is left handed or right handed.

Because it is important to figure the first hemisphere of the brain to activate through to the second, it has been found to be of significant value that the words be provided to the subject in writing so that there is a visual observation of the words from which inspiration is taken for the drawing.

While reference has been made to twelve specific symbols, a large amount of information can be obtained from an augmented number of these symbols. The words that identify these symbols, while the words chosen thus far are the simplest and most generic form of words identifying the symbol, can be modestly altered and of course so far as foreign languages are concerned, a selection of the closest appropriate word would be expected to work in the similar way.

It is possible for instance to have an augmented list of words identifying symbols which can comprise for instance hand, eye, tree, fish, star, spiral, half-circle and zig-zag.

DETAILED DESCRIPTION

Figure 1:
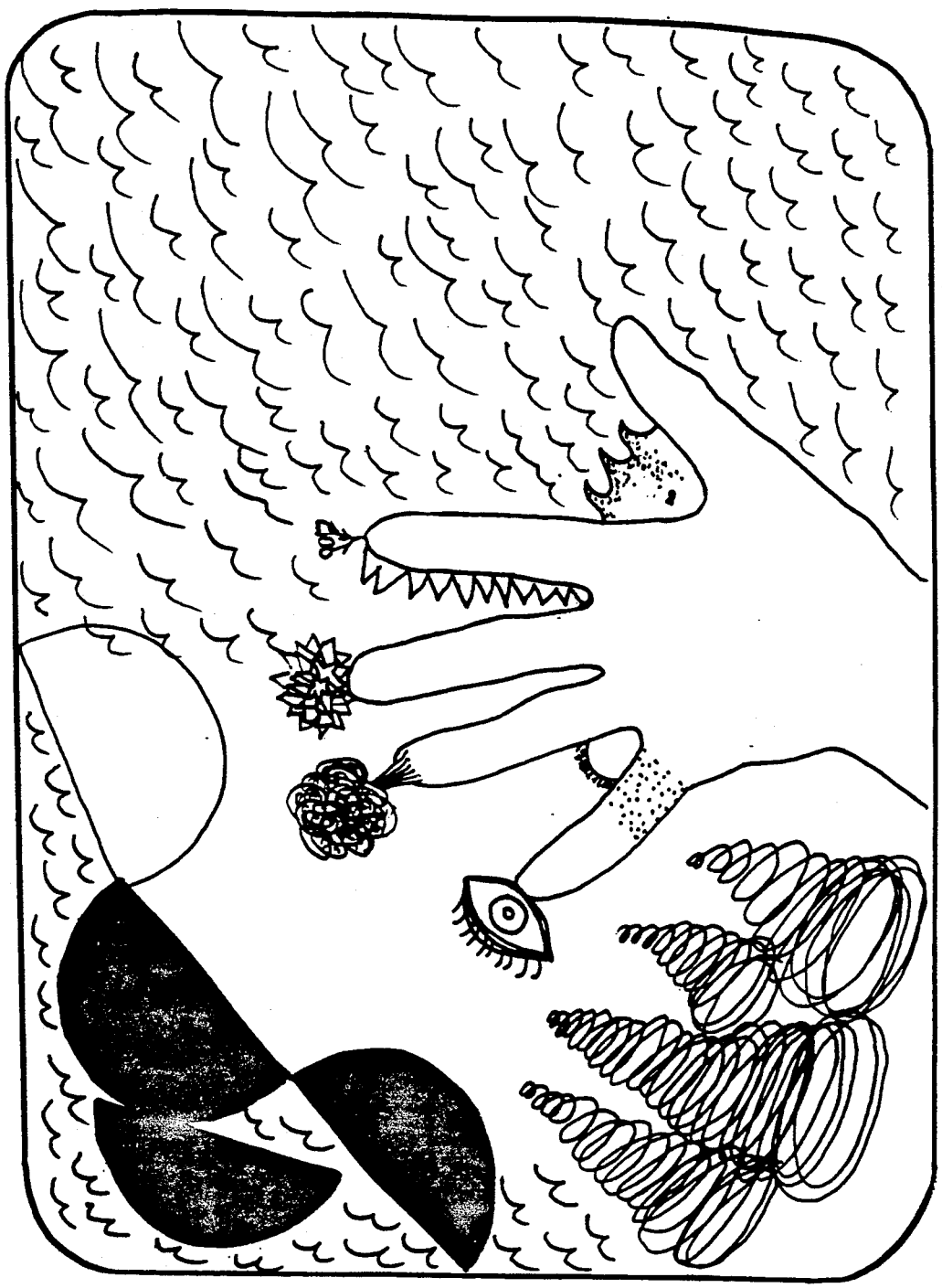
FIG. 1 replicates a representative drawing prepared by a subject under instruction of a person practicing the method of the present invention.

Some explanation will now be given as to the techniques by which interpretation can be made of drawings produced and in so giving the interpretation, a description of the preferred method of production of such drawing for a selected subject will also be given it being clear that it is not intended that such preferred embodiment should necessarily restrict the invention nor that the interpretation is presently other than for the purpose of illustrating the relevance and fundamental significance of the specific words chosen.

It is of course to be considered that while reference is made to the end result being an art work, it is not intended that the work should be considered a work of artistic merit which is quite incidental to the ability for a person to be able to interpret particular characteristics related to the subject from the drawing.

It is incidentally not considered to be a non-performance of the method if the subject does not follow the precise instructions for instance by not interconnecting one or more of the symbols with others as can be requested as one of the instruction requests. This apparently involuntary decision to provide such space separation or perhaps to leave out the symbol is a further characteristic of the drawing which can provide further assessment potential.

I am now going to briefly explain some of the involuntary traits that appear to be triggered and disclosed by these specific words.

The first is the hand.

A person's own hand is the object that a person sees most of, of ones own body and this is persistent and exists from birth to death.

Such an image therefore appears to become implanted as an identification of self and it appears in drawings to reflect both as itself and its relationship to other symbols as representing the self image of the subject.

Now referring to the eye.

Almost always the most noticeable characteristic of other people is their eyes.

The glare of disapproval arises from appearance of eyes, a smile is connected with the eye and if someone is feeling uncomfortable in another's presence, they avoid their "eyes".

The eye therefore has become connected with thoughts of the image of other people of authority in that the eyes are seen to be a mechanism of "control".

The relevance in a drawing of the eye, and its correlation with other symbols all go to providing an ability apparently to assess the position of authority of others or appreciation of others with respect to the subject self.

Now referring to the tree.

No other single image would appear to represent so clearly, a passive long standing respected life form which in so far that it provides the potential a root structure, a trunk and branches with leaves or no leaves and the history of the tree can be envisaged from the trunk all provide a strong connection with the concept of "growth". This particular form is well recognised by therapists.

A discovery has been in relation to this therefore that in drawing a tree under the simple instructions as described, there appears to be an involuntary effect of showing characteristics through the trunk and into the branches which provide an indication of the history of growth.

For instance, a person that suffered a very traumatic period in their early life will often show jagged forms across the middle of the trunk.

In a sense then the tree is found to represent a history of life growth.

We now refer to the "sun".

The common connection of "the sun" is in relation to "family or familial support".

The one common factor to all people throughout the world is the sun and warmth attached to the sun.

Warmth in a psychological sense is certainly the strongest connection with family support but many of the other more physical characteristics relate to warmth during caressing and hugging, warmth around the family fire and warmth experienced directly from the sun during periods out of doors.

In many instances it might be narrow to limit this to "family support" rather than simply the support from those in a close relationship.

Now we refer to the bird.

There is a well known cliche "free as a bird".

But once again, there is this absolutely common association with all people in the world with the bird as an animal that invariably has few negative connotations or negligible negative connotations, always appears to be able to keep itself relatively free from excessive human interference, and is strongly implanted apparently within the psyche as associated with "freedom".

Literature has many cliches which may strongly implicate this as well as for instance the well-known saying "freedom has gone through the window" when talking about someone who has lost their freedom, or the use of the word "flight" to indicate an escape.

Whatever the reasons for this, as with the other symbols, I have discovered this very strong correlation to the extent that when using the bird as a symbol, this would appear to correspond very strongly with peoples hopes and aspirations or experiences or present feelings with relation to their freedom or otherwise.

We now refer to the fish.

I have found that this symbol appears to be associated with basic drive/sexuality.

The fish being a universal concept also has characteristics such as slipperiness fluidity and sinuous movement which in real life can have an indirect but distinct association with sexuality.

Such examples as our language includes phrases like "catching a man". Prostitutes are known as "hookers". Basic elements of conception involve the swimming of the sperm.

We now look at the flower.

This symbol appears to be related to creativity as an expression of talent.

Once again, it is a common element that has been available through history which has been observable by all and exists in many varied forms. The flower has implications of attractiveness that leads to new creation, but is also a valued decorative and creative element in human affairs.

We now deal with the four abstract symbols the zig-zag, the spiral, wave and half-circle.

Referring specifically to the "zig-zag".

The interpretation that appears to occur with this is that it is an indication of stress, distress or pain.

Almost throughout all of nature, things which have been stressed or torn apart or torn asunder are left with jagged edges.

Perhaps one of the most frightening and traumatic experiences relates to being involved in a lightning strike which has the classical jagged shape.

The effect of water passing across the earth as in for instance the Grand Canyon also provides a zig-zag form which implies to some extent the effect of stress on the land.

We now deal with the half-circle.

This provides an apparent connection with either safety, as in shelter, lying low, feeling protected or openness, receptivity, change, dynamic movement, quest or even esoteric interest.

There is an interpretation as to whether the half-circle is open-side downwards or open-side upwards and these variously provide for instance with open-side downwards, the concept of an igloo, the hide-away, or something protective. When the half-circle is open side to either side of the paper, or at any angle this provides a concept of a shift, perhaps an exclusion action rather as brackets do in language structure.

With the open-side upward, there is the receptivity concept as in a cup to receive liquid nourishment.

We now deal with the spiral.

This is a very fundamental shape within our existance for instance, the very DNA molecule that is at the heart of human life follows a double helix shape.

The concept of a spiral in many cases relates energy and change either positive or negative and the large examples that can influence people in this regard are such nature occurrences as a whirlpool or perhaps more so, a tornado.

Water passing from a bath can disappear whilst following this whirlpool pattern and indeed all turbulence which is probably most often seen in wild seas also has strong elements of spirals.

Generally it is interpreted variously as "progression, development, effort, entropy, entrapment, dynamic change or destructive power".

An element in the interpretation is to whether a person has started the spiral from the beginning outwardly or from the outward going inward, or which elementary form the spiral assumes.

We finally now deal with the wave.

This concept appears to indicate the extent of interaction that a person may have experienced.

In other words, it appears to indicate the patterns of change in a person's life.

The wave is not only directly associated with waves as are seen at sea, but rather pulsations meaning cyclic occurrences.

For example this embraces waving goodbye, heat wave and crime waves.

This then finishes the very brief summary of the specific symbols.

Further interpretation can be gained by the extent to which the various symbols are combined so that an eye drawn in a very large manner on a fish might mean the sexual partner is associated with authority.

Zig-zag across a tree can indicate as a matter of history a substantial interruption or some traumatic event that has occurred within the subjects life thus far.

Further, some of the symbols appear to have a feminine aspect as compared to others having a masculine aspect so that further interpretation on this basis can also be gained.

These comments indicate the type of assessment that can be deduced and on work thus far carried out there has been a very high accuracy correlation with an interpretation that has been developed and a comparison of this with the subject afterwards.

There is still scope for significant developments but thus far the method has significant value for profile assessment for employment selection purposes.

In order to further better understand this invention two examples of drawings which have followed the method of the invention will now be referred to and a brief interpretation given in respect of each of these two drawings.

The drawing which was drawn by the subject who will be referred to as "Janette" is shown at FIG. 1.

The dominant parts of this drawing are the hand which is central and in a position which most strongly identifies self.

The myriad of birds illustrating freedom almost overwhelm other aspects but it is no single large bird but many smaller birds which suggests something more than freedom alone but rather perhaps freedom of others imposing to some extent.

The eye providing the concept of authority is linked quite closely to the hand but is also in a relatively clear space from the many birds suggests a separation of the authority perhaps from the many elements providing freedom.

The zig-zag along the index finger is usually associated with stress and this is associated with the self image. The fish indicating sexuality between the thumb and index finger is of an extremely small size and is subjugated within a wave like shape which indicates change.

The sun between the small finger and the next finger is again being associated closely with the hand, is predominantly covered and is interestingly alongside what appears a band-aid like cover of the little finger which suggests some feeling of damage or damage control. The two symbols indicating growth and life patterns emanate from two fingers that is the flower and the tree and these seem to be quite closely associated with the self and emanate from self suggesting that the person is a strong person to a large extent knowing her own mind and having her own ambitions in relation to the future.

The four semi-circles on the upper left hand side of the drawing are closely associated with protection or openness and it is noticed that three of these are darkly shaded and one is open and that two are upwardly facing and two are downwardly facing whereas one is off set to the remaining three. The strong association with family suggests that this could be indicative of a family situation and even be illustrative of a relationship in which the open half-circle is the subject herself and the remaining are husband and children and there does appear to be a problem here again because of the distorted positioning of at least one of those half-circles.

The strongly turbulent vortexes on the left hand bottom side suggest a build up of concern in relation to change and once again it is noticed that there are four of these and it would suggest that there is strong pressure building up in relation to some of four components or persons in relation to change.

As far as the correlation of this interpretation is concerned, it was subsequently established that the woman had the position of a Director at a child-care centre and her marriage was in strife at the time of the drawing and that she had two children.

Figure 2:
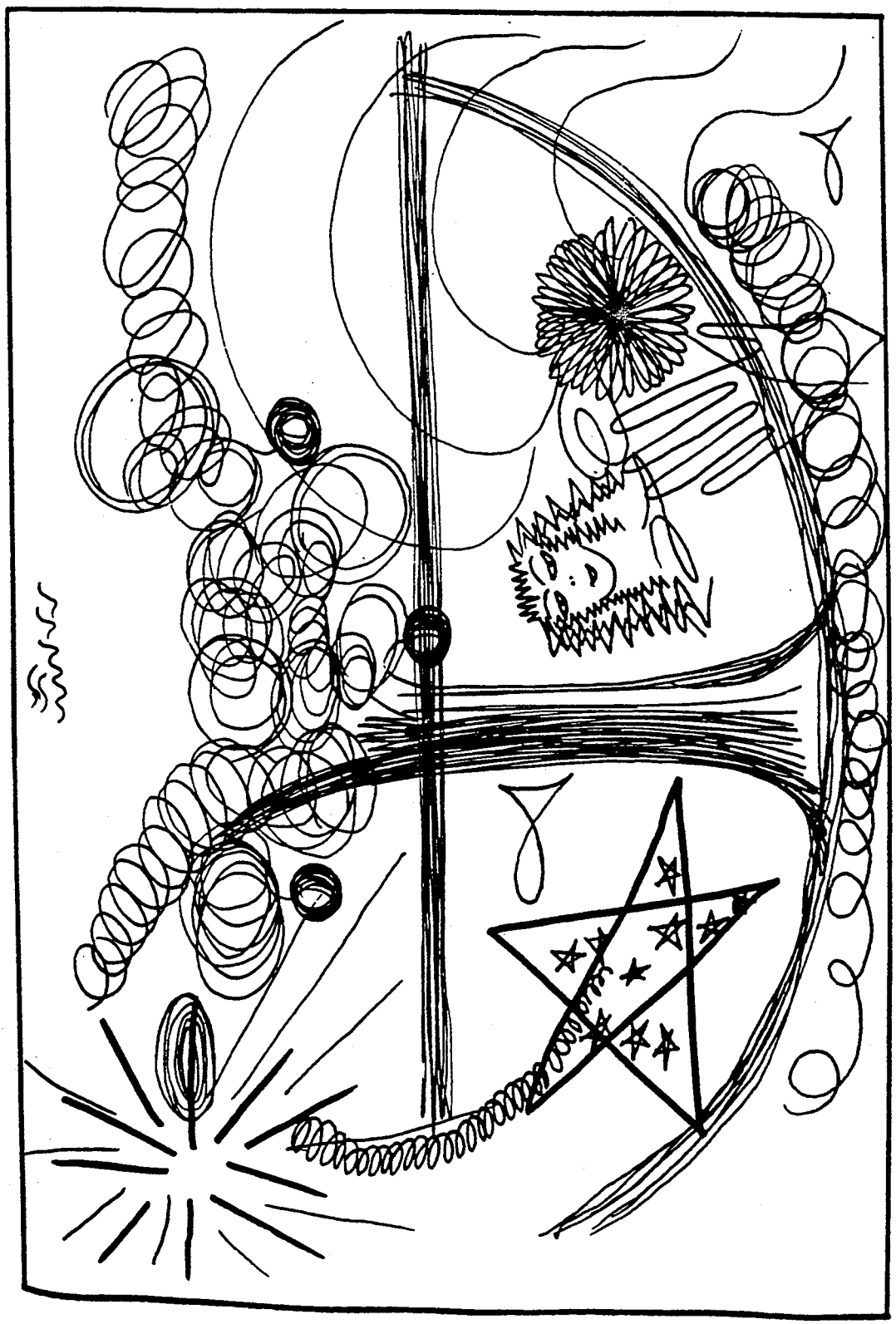
FIG. 2 replicates another such drawing.

Our next drawing which is to be referred "Lauren's drawing" is now referred to as FIG. 2.

This drawing is dominated by a heavily filled in tree trunk which terminates to the top with a very deeply impressed zig-zag suggesting a substantial crisis in the life path and there after a most un-tree like vortexes.

The tree has three balls hanging from it two on one side and one on the other which appear to be in a sense the fruits of the tree although a first of these appears to be just below or related to the stress line and the other two are somewhat higher.

On the right hand side there is a portrait with strongly outlined eyes and with a very strongly outlined zig-zag rendition.

Zig-zags being associated with stress suggest that this person feels under significant stress and is surrounded by stress.

There are two fish in the drawing one just to the left of the trunk and one of the right hand lower corner.

The one of the right hand lower corner is somewhat less dominant and seems to have a separated tail whereas the one of the left hand side is much more dominant and much more strongly drawn.

In its relationship with sex, this would suggest that perhaps there have been two dominant sexual partners one of which has been substantially subjugated and there is now a much more dominant single experience here.

The agent for change is the wave and this on the right hand side and this to some extent is intrusive into the open space defined by the upturned semi-circle in which the tree and a number of the other images are located.

The birds up in the top centre of the drawing are relatively misshapen and perhaps then are seen as relatively minor and albeit relatively important because of the position in the drawing, are perhaps a goal which is going to be difficult.

On the left hand top is a sun which is almost starkly empty but explosive so that there is almost no central warmth. Emanating from the sun is a spiral terminating in a star which is very dominant within the total drawing the star illustrating ambition.

This appears to be relatively strong and intending to be dominant and many small stars suggest multiple ambitions so that there is strong hope.

The image itself illustrated by the hand is subjugated within many other parts of the drawing and the hand drawing itself is not a strong one in which the fingers are unduly extended.

This suggests a relatively weak self image and perhaps to some extent an injured self image which could perhaps bear strengthening.

The underlying spiral terminating in the change aspect of the wave suggest a relative turbulent period as existed.

One interesting aspect of the drawing of the foliage of the tree is up on the left hand side is a small image that perhaps is a bird but it is somewhat overdrawn so that something is emerging but it is not clear what.

There is a relatively strong line starting relatively vertically from the tree trunk and then pushing out to this.

The correlation is that the woman was a very busy mother with 12 year old twins of a first marriage and a small son of her second marriage.

When the drawing was done, the woman was pregnant again and expecting twins.

The interpretation suggesting birth from the trees of objects seems to correlate very closely to children that have been born and are about to be born.

The strong zig-zag faction in the tree trunk also clearly indicates a stressed period in this person's life.

The other factors noticed appear to correlate reasonably closely to the subsequently discovered characteristics.

The two illustrated examples illustrate the way in which an interpretation based upon the earlier reasoning can be used but it depends upon a clear understanding of the meanings that the mind seems to apply to certain symbols but then provides this inter-relationship that is beyond the conscious wish of the person who is drawing the drawing.

It has been observed that it does not appear to be of concern that a person asked to do a drawing knows that basis upon which the interpretation will be made and that this does not appear to change a substantial effectiveness for testing purposes of a drawing.

Through a number of examples that have now been worked on, the correlation appears to be very substantial between the symbols and the interpretation that can be gained from such symbols.

A drawing itself is a complex inter-relationship of the symbols and each symbol itself is changed and is different in each drawing so that there is a significant additional input in relation to a person's own creativity.

However, it would appear to offer a very useful technique for gaining further psychological insight into any subject person.

I claim:

1. A method of psychological testing of a person, comprising:
    (a) instructing the person to produce a drawing which includes at least one pictorial representation of each of at least a majority of the following items: a hand, an eye, a tree, a fish, a star, a spiral; a half-circle, and a zig-zag; and
    (b) subjecting to psychological interpretation the drawing produced in response to step (a).

2. The method of claim 1, wherein:
said items further include a flower, a bird, the sun and a wave.

3. The method of claim 1, wherein:
in conducting a step (a), the person is instructed to interconnect said pictorial representations while producing said drawing.

4. The method of claim 1, wherein:
in conducting step (a), the person is instructed to produce said drawing using a specific medium, which medium produces markings that vary in heaviness depending on pressure exerted thereon by the person while producing said drawing.

5. The method of claim 4, wherein:
in conducting step (a), the person is instructed to produce said drawing using a pencil as said medium.

6. The method of claim 1, wherein:
in conducting step (a), the person is instructed to add said pictorial representations to said drawing in a predetermined sequence.

7. The method of claim 1, wherein:
in conjunction with conducting step (a), a notation is made for use in step (b) as to which of their left hand and right hand is used by the person for producing said drawing.

8. The method of claim 1, wherein:
in conjunction with conducting step (a), a notation is made for use in step (b) as to the sequence in which the person adds said pictorial representation to said drawing.

9. The method of claim 1, wherein:
in conducting step (a), said person is instructed orally to produce said drawing.

* * * * *